United States Patent [19]
Veronesi et al.

[11] Patent Number: 6,107,277
[45] Date of Patent: Aug. 22, 2000

[54] CALCITONIN SALMON ANALOGUES

[75] Inventors: Paolo Alberto Veronesi; Emanuela Peschechera, both of Milan; Anna Maria Veronesi, Umbra, all of Italy

[73] Assignee: Therapicon S.R.L., Milan, Italy

[21] Appl. No.: 08/907,602

[22] Filed: Aug. 8, 1997

Related U.S. Application Data

[63] Continuation of application No. PCT/EP96/00487, Feb. 2, 1996.

[30] Foreign Application Priority Data

Feb. 8, 1995 [EP] European Pat. Off. .............. 95101681
Nov. 15, 1995 [GB] United Kingdom ................... 9523442

[51] Int. Cl.$^7$ .............................. A61K 38/23; C07K 1/00
[52] U.S. Cl. ........................... 514/12; 530/307; 530/345; 436/86
[58] Field of Search ............................... 514/12; 530/307, 530/345; 436/86

[56] References Cited

U.S. PATENT DOCUMENTS 3,926,938  12/1975  Hughes et al. ....................... 260/112.5

FOREIGN PATENT DOCUMENTS

| | | |
|---|---|---|
| 0 302 772 B1 | 2/1989 | European Pat. Off. . |
| 0 327 756 B1 | 8/1989 | European Pat. Off. . |
| 0 364 235 A1 | 4/1990 | European Pat. Off. . |
| 0 468 182 A1 | 1/1992 | European Pat. Off. . |
| 0 471 618 A1 | 2/1992 | European Pat. Off. . |
| 2 127 689 | 4/1984 | United Kingdom . |
| 2184729 | 7/1987 | United Kingdom . |
| WO 93/06854 | 4/1993 | WIPO . |
| WO 94/08622 | 4/1994 | WIPO . |

OTHER PUBLICATIONS

Abstract JP 1230530.
Abstract J03052821.
Abstract EP 156772.
Abstract JP 63316737.
Database Toxlit on STN, No. 1972:33662 Toxit; Barlet JP, 'Effects of Procin, Salmon, and human calcitonin on urinary excretion of some eclectrolytes in sheep', J. Endocrinology (abstract), 1972.
Database EMBASE on STN, No. 74005418 Embase; Garijo et al. 'Effects of treatment with caliconin in case of myeloma lgG with hypercalcima and hyperuricemia', Rev. Clin. Esp. (abstract), 1973.
Database MARPAT on STN, No. 124:30425 Marpat; Datsumata et al., JP 07188297, Jul. 25, 1995.

*Primary Examiner*—Cecilia J. Tsang
*Assistant Examiner*—Anish Gupta
*Attorney, Agent, or Firm*—Steven P. Shurtz; Brinks Hofer Gilson & Lione

[57] ABSTRACT

Salcatonin (i.e. salmon calcitonin) analogues of formula R1-Ser-Asn-Leu-Ser-Thr-Cys(SR2)-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH2 (I) are disclosed, in which R1=-Cys-S—H, -Cys—OH, -Cys-S-ether or -Cys-S-ester (where the ether or ester residue has 2–5C) or a corresponding salt or isomer; R2=H, OH, ester or ether residue of 2–5C or acetamidomethyl, or a corresponding salt or isomer.

15 Claims, 1 Drawing Sheet

CALCITONIN SALMON ANALOGUES

CROSS REFERENCE TO RELATED APPLICATION

This application is a continuation of PCT Application Ser. No. PCT/EP96/00487, filed Feb. 2, 1996, designating the United States of America.

This invention relates to novel substituted salmon calcitonin (salcatonin) analogues. More particularly this invention relates to salcatonin analogues, which are useful for the prevention or treatment of diseases such as osteoporosis, hypercalcemia, Paget's disease, as reference for analytical testing, and to methods of production and use thereof.

Salcatonin and its preparations, having hypocalcemic properties, are disclosed in the following documents:

| | |
|---|---|
| GB Pat. No. 82-28390 | Oct. 05, 1982 |
| GB Pat. No. 84-7907 | Mar. 27, 1984 |
| JP Pat. No. 63316737 | Dec. 26, 1988 |
| EP Pat. No. 302772 | Feb. 08, 1989 |
| EP Pat. No. 327756 | Aug. 16, 1989 |
| JP Pat. No. 1230530 | Sept. 14, 1989 |
| EP Pat. No. 364235 | Apr. 18, 1990 |
| JP Pat. No. 03052821 | Mar. 07, 1991 |
| EP Pat. No. 91109497 | June 10, 1991 |
| EP Pat. No. 471618 | Feb. 19, 1992 |
| WO Pat. No. 9306854 | Apr. 15, 1993 |
| WO Pat. No. 9408622 | Apr. 28, 1994 |

The prior art documents are all concerned with calcitonin salmon (salcatonin) raw material and its preparations, having hypocalcemic properties.

The calcitonin salmon molecule is characterized by a S—S bridge between the Cysteine in position 1 and the Cysteine in position 7. The applicants for the present invention have surprisingly found that analogues of calcitonin salmon molecule having the disulphide bridge between the positions 1 and 7 broken, with the possibility of introduction of various substituents confers significant advantages in terms of hypocalcemic activity and use as analytical agents.

Figure 1:
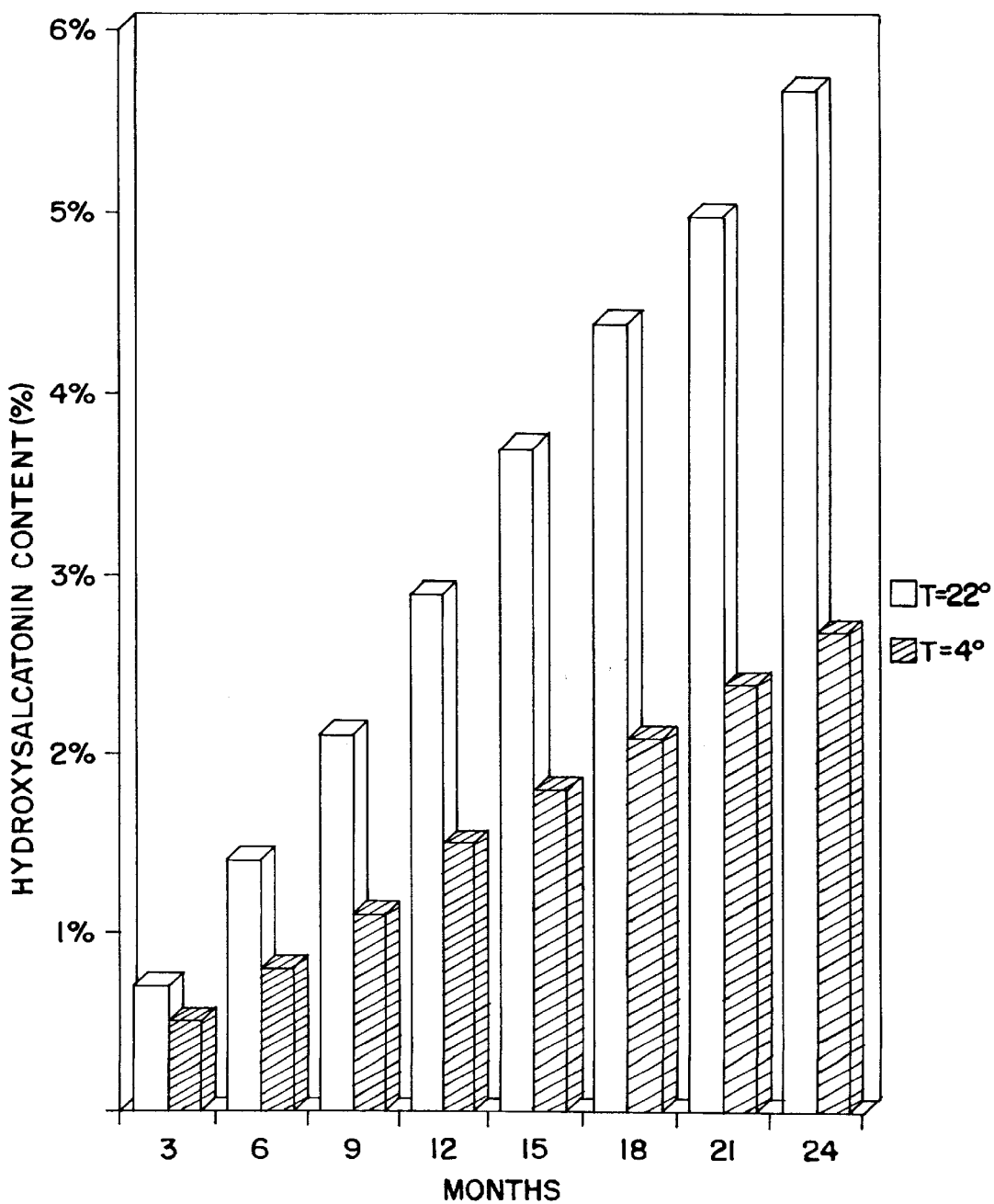
FIG. 1: A graph illustrating the age of the tested salcatonin preparation in the range of 24 months.

The novel salcatonin analogues of this invention, useful as hypocalcemic agents, substituted as 31 or 32 amino acids, are represented by the following formula:

FORMULA I

SEQ. ID NO. 1.

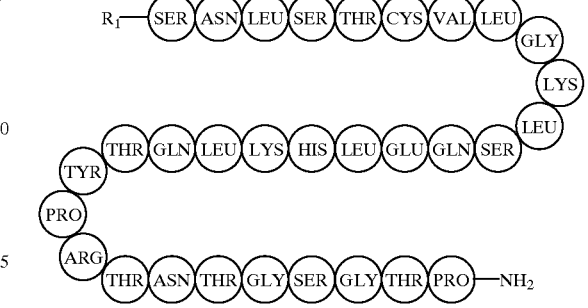

wherein $R_1$ is -Cys-SH or Cys-S-OH: or -Cys-S-ether or -Cys-S-ester wherein the ether or ester has from 2 to 5 carbon atoms or pharmaceutically acceptable salts or isomers thereof; $R_2$ is —H, —OH, an ester or ether having from 2 to 5 carbon atoms or, pharmaceutically acceptable salts or isomers thereof.

Preferably $R_1$ and $R_2$ are as follows:

| COMPOUNDS | $R_1$ | $R_2$ |
|---|---|---|
| Compound 1 | —Cys—SH | —OH |
| Compound 2 | —Cys—S—OH | —H |
| Compound 3 | —Cys—SH | —OOC—CH$_3$ |
| Compound 4 | —Cys—SH | —OOC—C$_2$H$_5$ |
| Compound 5 | —Cys—SH | —OOC—C$_3$H$_7$ |
| Compound 6 | —Cys—SH | —OOC—C$_4$H$_9$ |
| Compound 7 | —Cys—S—OOC—CH$_3$ | —H |
| Compound 8 | —Cys—S—OOC—C$_2$H$_5$ | —H |
| Compound 9 | —Cys—S—OOC—C$_3$H$_7$ | —H |
| Compound 10 | —Cys—S—OOC—C$_4$H$_9$ | —H |
| Compound 11 | —Cys—SH | —O—C$_2$H$_5$ |
| Compound 12 | —Cys—SH | —O—C$_3$H$_7$ |
| Compound 13 | —Cys—SH | —O—C$_4$H$_9$ |
| Compound 14 | —Cys—SH | —O—C$_5$H$_{11}$ |
| Compound 15 | —Cys—S—O—C$_2$H$_5$ | —H |
| Compound 16 | —Cys—S—O—C$_3$H$_7$ | —H |
| Compound 17 | —Cys—S—O—C$_4$H$_9$ | —H |
| Compound 18 | —Cys—S—O—C$_5$H$_{11}$ | —H |

Compounds 1 and 2 or their mixture are also conventionally defined hereinafter as hydroxysalcatonins.

Preferred embodiments of the present invention are (i) when $R_1$ is —Cys—S—OH or an ester $R_2$ is a hydrogen atom, or (ii) when $R_2$ is =-OH or an ester, $R_1$ is -Cys-H.

This invention also includes pharmaceutically acceptable salts of any suitable inorganic or organic acids. Suitable inorganic acids are, for example, hydrochloric, hydrobromic, sulfuric and phosphoric acids.

Suitable organic acids include carboxylic acids such as acetic, propionic, glycolic, lactic, pyruvic, malonic, succinic, fumaric, malic, tartaric, citric, ascorbic and maleic acids.

The above salts may be prepared by conventional means, already well known to a person skilled in the art.

It has now been surprisingly discovered that the compounds of this invention are useful as hypocalcemic agents, inhibiting physiological or pathological bone re-absorption.

In fact the inhibition of bone re-absorption may be determined by a decrease of urinary excretion of hydroxyproline and that associated with the reduction of high and pathological serum levels of alkaline phosphatase and with the normalization of calcium balance, promotes collagen and bone tissue rebuilding, reducing the total blood content of $Ca^{2+}$ after some months of treatment.

Moreover salcatonin analogues exert antalgical action, reducing partially or entirely the pain.

Salcatonin analogues may be used in Paget's disease (osteitis deformans), hypercalcaemia caused by cancers, hyperparathyroidism, intoxication of Vit. D, both as emergency treatment and prolonged as well, osteoporosis of different origin, optionally combined with other associated therapy, specific for each unhealthy condition and Sudeck's disease.

In order to evaluate the pharmacological activity of salcatonin analogues, a preliminary screening by biological assay was carried out, as indicated in BP (British Pharmacopoeia) 1993 Volume I, page 587, using three different dosages (8 mI.U./rat, 16 mI.U/rat, 32 mI.U./rat), obtaining the following results, reported hereby, expressed as average value of three determinations:

| COMPOUND | | AVERAGE VALUE (mg Ca %) |
|---|---|---|
| Compound 1 | ($R_1$ = Cys—SH; $R_2$ = —OH) | 4.62 |
| Compound 2 | ($R_1$ = Cys—S—OH; $R_2$ = —H) | 4.48 |
| Compound 3 | ($R_1$ = Cys—SH; $R_2$ = —OOC—$CH_3$) | 2.65 |
| Compound 4 | ($R_1$ = Cys—SH; $R_2$ = —OOC—$C_2H_5$) | 2.83 |
| Compound 5 | ($R_1$ = Cys—SH; $R_2$ = —OOC—$C_3H_7$) | 2.51 |
| Compound 6 | ($R_1$ = Cys—SH; $R_2$ = —OOC—$C_4H_9$) | 2.19 |
| Compound 7 | ($R_1$ = Cys—S—OOC—$CH_3$; $R_2$ = —H) | 2.32 |
| Compound 8 | ($R_1$ = Cys—S—OOC—$C_2H_5$; $R_2$ = —H) | 2.56 |
| Compound 9 | ($R_1$ = Cys—S—OOC—$C_3H_7$; $R_2$ = —H) | 2.78 |
| Compound 10 | ($R_1$ = Cys—S—OOC—$C_4H_9$; $R_2$ = —H) | 2.07 |
| Compound 11 | ($R_1$ = Cys—SH; $R_2$ = —O—$C_2H_5$) | 2.87 |
| Compound 12 | ($R_1$ = Cys—SH; $R_2$ = —O—$C_3H_7$) | 2.62 |
| Compound 13 | ($R_1$ = Cys—SH; $R_2$ = —O—$C_4H_9$) | 2.57 |
| Compound 14 | ($R_1$ = Cys—SH; $R_2$ = —O—$C_5H_{11}$) | 2.74 |
| Compound 15 | ($R_1$ = Cys—S—O—$C_2H_5$; $R_2$ = —H) | 2.91 |
| Compound 16 | ($R_1$ = Cys—S—O—$C_3H_7$; $R_2$ = —H) | 2.85 |
| Compound 17 | ($R_1$ = Cys—S—O—$C_4H_9$; $R_2$ = —H) | 2.23 |
| Compound 18 | ($R_1$ = Cys—S—O—$C_5H_{11}$; $R_2$ = —H) | 2.46 |

The compounds of the present invention are advantageously formulated in liquid forms such as solutions or suspensions administrable for parenteral route, nasal spray or as rectal capsules.

The injectable dosage forms are solutions or suspensions of the above compounds in a suitable pharmaceutical carrier, which is a sterile liquid such as water with or without the addition of other pharmaceutically acceptable excipients or adjuvants.

For use as nasal spray, the solution or suspension of salcatonin analogues of this invention may be formulated as aqueous preparations with or without convenient excipients, packed in suitable containers equipped with pressurized inhalers or nebulizing or atomizing—dosing pumps.

The recommended daily dose of novel compounds described herein may quantitatively vary over a wide range of from 10 I.U. to 400 I.U., more preferably from 100 I.U. to 200 I.U., in order to provide in a unit dosage an effective amount of active analogue.

As used herein the term "I.U." refers to the appropriate International Reference Preparation (I.R.P.) of human, salmon, porcine, eel calcitonins established by the National Institute for Biological Standards and Control, Blanche Lane, South Mimms, Potters Bar, Hertfordshire, E6 30G, U.K.

Another preferred embodiment of the present invention is that the novel compounds, more specifically hydroxysalcatonins, may be advantageously used as selective and practical indicators or markers to determine the age and consequently the shelf-life of salcatonin preparations.

In fact it was also surprisingly discovered that salcatonin solutions, due to their instability in the presence of oxygen ($O_2$) at room temperature, progressively degrade producing appreciable quantities of hydroxysalcatonins.

When the solutions are exposed to $O_2$, the degradation process is so fast, that remarkably variable (inconstant) quantities of hydroxysalcatonins are produced, so that it is difficult to establish any relationship between hydroxysalcatonins content and the age of the salcatonin preparation.

For these reasons it is preferred that manufacture of salcatonin solutions is carried out under saturated nitrogen atmosphere (about $1 \times 10^5$ Pa (1 bar)), in order to reduce the degradation process. It is also preferred the material is stored under refrigerated temperature conditions.

In order to establish the linearity of the degradation process involving salcatonin preparations, analytical test conditions have been standardized and experimental samples have been prepared with an oxygen content $\leq 1$ p.p.m. and stored separately either at temperatures of from 4° to 8° C. or at 22° C.

Under these conditions it has been unexpectedly demonstrated that it is possible to determine the age and consequently the shelf-life of a salcatonin preparation once the quantity of hydroxysalcatonins, produced during the storage period, is analytically determined, using the synthetized hydroxysalcatonins of the invention as reference standards.

In fact the enclosed Graph 1, shows analysis of the content of hydroxysalcatonins at different intervals on six batches of salcatonin preparations (ampoules 100 I.U./ml), demonstrates a good linearity between the age of the formulations and the above reference standard, thus representing a practical and suitable parameter for the assessment of their shelf-life.

Hydroxysalcatonins are synthetized from salcatonin (batch No. 6Q1, branded UCB-Bioproducts, Belgium) by an oxidation process using suitable oxidizing agents, such as $H_2O_2$, performic acid, percloric acid, $O_3$, chloranil or an equivalent thereof, to open the disulphur bridge between cysteines 1–7 of salcatonin and then oxidize preferably cysteine in position 1, while small quantities of oxidized cysteine in position 7 may also be obtained.

The first step is carried out in a flask, where salcatonin is completely dissolved in suitable dilute acids and anhydrous methanol is added with stirring, in order to prevent freezing of the solution during oxidation.

The salcatonin solution and the oxidizing agent are transferred to the separate arms of a glass stoppered test-tube to which a side arm has been sealed.

The reagents are cooled during 30 minutes in a bath maintained from −7° C. and −10° C. (or at 0° C.) and then mixed by tipping the tube.

The reaction is allowed to take place at the same controlled temperature for approximately 2.5 hours.

The obtained hydroxysalcatonins are then purified on a conventional separatory column containing a suitable resin (Spherisorb™ $C_{18}$, 250×4.6 mm, 5µ) and, once the solution has been chromatographed and hydroxysalcatonins separated from the mixture of salcatonin and other potential related substances, the synthetized analogues are mobilized from the corresponding portion of the resin by using acetonitrile, as a solvent.

Acetonitrile is then completely removed from the solution containing hydroxycalcitonins by using conventional methods.

In order to use hydroxysalcatonins as a reference standard for analytical tests, stock solutions of the same in water are prepared, kept frozen at about −80° C., lyophilized and used no longer than 6 months from their preparation.

Just before use, the lyophilized hydroxysalcatonins are admixed to the same suitable vehicle as that of the sample to analyze, in order to obtain an adequate reference standard solution.

This standard at known concentration is then injected in an HPLC/MS system, thus obtaining calibration graphs, which are later on used to identify the peaks and to determine quantitatively the hydroxysalcatonins in the stored salcatonin solutions, in order to assess the exact age of the tested preparations by comparing them with the standard graph.

Analytical determinations are carried out with a Perkin Elmer Mass Spectrometer Sciex API III equipped with an "Ion-spray" ionizations source.

The mass Spectrometer is connected to an Applied Biosystems 140A syringe HPLC with a Perkin Elmer ISS-101 autosampler.

The column is eluted with a gradient indicated hereby:
(A) acetonitrile+0.1% trifluoroacetic acid (TFA)
(B) water+0.1% TFA.

The microbore column is eluted at 50 $\mu$l/min.

The gradient begins with 10' in isocratic conditions at 100% B followed by a first linear step that takes to an 80% of B in 5' and by a second linear step that reaches the 50 % of B in 20'; this condition is then isocratically maintained for 15'. For the analysis on microbore column the different samples of salcatonin preparations under testing are injected without extraction or clean-up steps; the volume of each injection is 500 $\mu$l.

For the reference standard the injections are of the same volume from solutions at 100 ng/ml prepared with lyophilized product dissolved in the same solvent mixture of the samples, just before use.

HPLC-MS analyses are carried out on-line during chromatographic separations on microbore column without splitting.

MS analyses are performed in scanning mode, range from m/z 400 to 2000, acquiring positive ions.

Some samples are then analyzed with MS/MS techniques using argon as collision gas (collision gas thickness $3\times10^4$ atoms/cm$^3$) with a collision energy of from 50 to 200 eV.

In order to obtain quantitative determinations of hydroxysalcatonins with higher sensitivity and accuracy, the instrument is then operated in selected ion monitoring, choosing m/z values characteristic of the above products.

The results of the above analytical test (see Graph 1) demonstrate that hydroxysalcatonins are essential and suitable indicators to evaluate the age of salcatonin solutions, once they are prepared in nitrogen atmosphere and stored under controlled temperature conditions.

In fact the above results evidence a clear linearity between the content of hydroxysalcatonin(s) and the age of the analyzed samples.

The invention is further illustrated by the following examples, but in any case they are given by way of illustration only and are not to be construed as limiting the invention either in spirit or in scope as many modifications will be apparent to those skilled in the art.

EXAMPLE 1

Synthesis process of hydroxysalcatonins.

200 mg of salcatonin (batch No. 6Q1, UCB-Bioproducts, Belgium) was completely dissolved in 5.0 ml of formic acid (99%) and then 1.0 ml of anhydrous methanol was added.

Performic acid was prepared separately by adding 0.50 ml of 30% $H_2O_2$ to 9.5 ml of 99% of formic acid and the resulting solution was placed at room temperature (25° C.) for 2 hours in a stoppered flask.

The salcatonin solution and the performic acid were transferred to separate arms of a glass-stoppered test-tube to which a side arm is sealed.

Both reagents were cooled for approximately 30 minutes in a bath maintained at a temperature of from −7° C. to 10° C. and then mixed together by tipping the tube.

The reaction took place at a steady temperature for approximately 2.5 hours.

The obtained hydroxysalcatonins were purified using the following preparative method:

| Equipment: | 5060B Varian HPLC connected to a Gilson pump (Model 302) for the injection of the sample. |
|---|---|
| Column: | Spherisorb ™ $C_{18}$ (250 × 4.6 mm, 5$\mu$) |
| Eluent: | Gradient formed by: |
| | A) acetonitrile + 0.1% trifluoroacetic acid (TFA) |
| | B) water + 0.1% TFA |
| Flow rate: | 1 ml/min |

The hydroxysalcatonins were mobilized from the relevant portion of the column by using acetonitrile, which was then completely removed from the solution by conventional methods already well known in the art. A yield of 72.7% was obtained.

EXAMPLE 2

Preparation of 5,000 ampoules of hydroxysalcatonins (0.02 mg/ml). 1 ml of solution containing:

| Hydroxysalcatonins | 0.02 mg |
|---|---|
| Glacial acetic acid | 2.00 mg |
| Sodium acetate trihydrate | 2.00 mg |
| Sodium chloride | 7.50 mg |
| Water for injections | 1.00 mg |

Approximately 4.5 liters of water, for injections was introduced into a stainless steel dissolutor, previously sterilized and depyrogenated by steam and then cooled at about 8° C. The dissolutor was equipped with a stirrer and hermetically sealed under controlled bacteriological conditions by introducing filtered sterile nitrogen.

Sodium acetate trihydrate and glacial acetic acid were added under constant and slow stirring until complete dissolution of the ingredients.

The pH of the buffer solution was measured to be in the range of 4.2±0.3.

The total quantity of hydroxysalcatonins were dissolved separately in a 25 ml sterile and apyrogen Erlenmayer flask by introducing about 5 ml of cold buffer solution, thus obtaining the mother solution of hydroxysalcatonins.

Once the hydroxysalcatonins were completely dissolved the mother solution of hydroxysalcatonins, was added under constant and slow stirring to the base solution.

The remaining water for injectable preparations was added to the dissolutor to yield 5 Kg of solution and the pH was checked again (to be between pH 4.2±0.3).

The obtained solution was then sterilized by filtration, using a pre-cartridge 0.45 $\mu$m pore size (brand PALL), followed by a second cartridge 0.22 $\mu$m pore size (brand PALL) and finally was automatically divided in ampoules each containing 1 ml.

EXAMPLE 3

Preparation of 2,000 nasal spray bottles. (0.9 ml; 0.02 mg/ml) of hydroxysalcatonins.

1 ml of the solution containing:

| | |
|---|---|
| Hydroxysalcatonins | 0.02 mg |
| Sodium citrate dihydrate | 12.36 mg |
| Citric acid monohydrate | 12.11 mg |
| Sodium taurocolate | 10.00 mg |
| Disodium edetate | 1.00 mg |
| Benzalkonium chloride | 0.23 mg |
| Distilled water | 1.00 mg |

1.0 kg of distilled water was placed in a sterilized stainless steel container hermetically sealed, under controlled bacteriological conditions by introducing filtered sterile nitrogen.

A solution (A) was prepared separately in about 0.5 liter of distilled water to contain:

| | |
|---|---|
| Sodium citrate dihydrate | 24.72 g |
| Citric acid monohydrate | 24.22 g |
| Sodium taurocolate | 20.0 g |
| Disodium edetate | 2.0 g |

Once the above solution had been completely dissolved, the pH value was checked to be in the range of from 3.6 to 4.5 and it was added to the water into the dissolutor.

Under constant and slow stirring 0.46 g of benzalkonium chloride was added.

The total quantity of hydroxysalcatonins was dissolved separately in 50 ml of solution (A) in an volumetric flask, thus obtaining the mother solution of hydroxysalcatonins.

Once the hydroxysalcatonins were completely dissolved, the mother solution was added to the dissolutor under constant and slow stirring and the remaining water (about 0.5 liter) was introduced until to yield 2 liters of volume.

The obtained solution was filtered through a sterilizing filter (brand PALL, 0.22μ) and closed by the automatic filling operation into nasal spray bottles containing each 0.9 ml of solution.

EXAMPLE 4

Preparation of 4,000 nasal spray bottles (1.3 ml, 0.07 mg/ml) of compound 12. 1 ml of solution containing:

| | |
|---|---|
| Compound 12 | 0.07 mg |
| Sodium chloride | 6.00 mg |
| Sodium citrate dihydrate | 4.63 mg |
| Citric acid monohydrate | 3.00 mg |
| Methyl p-hydroxybenzoate | 1.30 mg |
| Propyl p-hydroxybenzoate | 0.20 mg |
| Sodium acetate | 1.00 mg |
| Alkylamidopropylbetain | 0.20 mg |
| Bidistilled water | 1.00 ml |

The bidistilled water (2.6 liters) was placed in a sterilized stainless steel container hermetically sealed, introducing filtered sterile nitrogen, in order to maintain the controlled bacteriological conditions.

A solution (A) was prepared separately in about 1.3 liters of bidistilled water to contain:

| | |
|---|---|
| Sodium chloride | 31.20 g |
| Sodium citrate dihydrate | 24.07 g |
| Citric acid monohydrate | 15.60 g |
| Sodium acetate | 5.20 g |

After the preparation of the above solution, the pH was checked to be in the range of from 4.2±0.5 and it was added to the water into the dissolutor.

Under constant and slow stiring 6.76 g of methyl p-hydroxybenzoate, 1.04 g of propyl p-hydroxybenzoate and 1.04 g of alkylamidopropylbetain were added.

Compound 12 (364 mg) was dissolved separately in 455 ml of solution (A) in a volumetric flask, thus obtaining the mother solution of compound 12, which was added to the dissolutor under constant and slow stirring.

The remaining water (about 845 ml) was introduced to yield 5.2 liters of solution.

The resulting solution was filtered through a sterilizing filter (brand PALL, 0.22 μm) and dispensed into nasal spray bottles containing each 1.3 ml of solution, by using conventional automatic filling.

While only certain embodiments of our invention have been described in specific detail, it will be apparent to those skilled in the art that many other specific embodiments may be practised and many changes may be made all within the spirit of the invention and the scope of the appended claims.

EXAMPLE 5

Chromatographic analytical determination of the age of a salcatonin preparation (stored at 4°–8° C. temperature), using synthetic hydroxysalcatonins as indicator of the degradation process.

Prepare a reference standard solution of pure hydroxysalcatonins having a concentration of 10 ng/ml, by dissolving in 10 ml of distilled water 100 ng of lyophilized hydroxysalcatonins, already synthetized as indicated in Example 1.

Use the salcatonin preparation under testing as it is, without extraction or clean-up steps.

The utilized HPLC/MS system is the following:

| | |
|---|---|
| HPLC | |
| Equipment: | Applied Biosystems 140A syringe HPLC with a Perkin Imer ISS—101 autosampler |
| Eluent: | (A) acetonitrile + 0.1% trifluoroacetic acid<br>(B) water + 0.1% trifluoroacetic acid |
| Flow rate: | 50 μl/min. |
| Injection volume | 500 μl |
| MS | |
| Equipment: | Perkin Elmer Mass Spectrofotometer Sciex API III equipped with an on-spray ionization source. |
| m/Z range: | 400–2000 m/z |
| Collision gas: | argon |
| Thickness collision gas: | $10^4$ atoms/$cm^3$ |
| Collision energy | 50–200 eV. |

From the HPLC/MS study, the tested salcatonin preparation presented a total hydroxysalcatonins content of 1.46%, compared with the reference standard.

Using the above figure of hydroxysalcatonins total content as an indicator for the degradation processes, it is possible to determine on the calibration Graph 1 the age of the tested salcatonin preparation in the range of 12 months.

What is claimed is:

1. A salcatonin analogue of the formula:

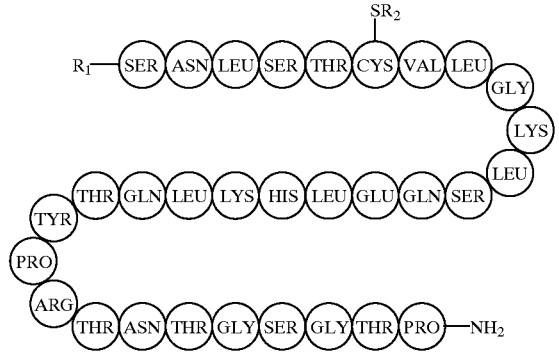

wherein $R_1$ is -Cys-S-H or -Cys-S-OH or -Cys-S-ester or Cys-S-ether wherein the ester or ether has from 2 to 5 carbon atoms or pharmaceutically acceptable salts or isomers thereof and $R_2$ is hydrogen or hydroxy or an ester or an ether having from 2 to 5 carbons atoms or a pharmaceutically acceptable salt of isomer thereof, provided that when $R_1$ is -Cys-S—H, then $R_2$ is not hydrogen.

2. A salcatonin analogue of the formula:

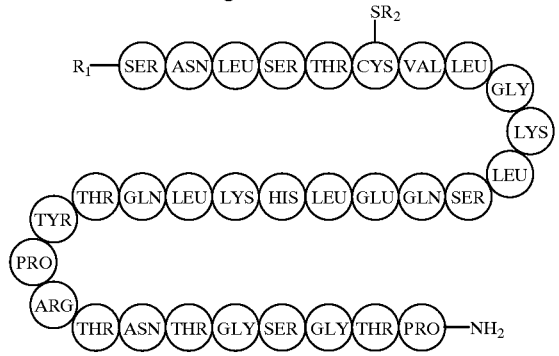

Where $R_1$ and $R_2$ are selected from the following:

| COMPOUNDS | $R_1$ | $R_2$ |
| --- | --- | --- |
| Compound 1  | —Cys—SH           | —OH |
| Compound 2  | —Cys—S—OH         | —H |
| Compound 3  | —Cys—SH           | —OOC—CH$_3$ |
| Compound 4  | —Cys—SH           | —OOC—C$_2$H$_5$ |
| Compound 5  | —Cys—SH           | —OOC—C$_3$H$_7$ |
| Compound 6  | —Cys—SH           | —OOC—C$_4$H$_9$ |
| Compound 7  | —Cys—S—OOC—CH$_3$ | —H |
| Compound 8  | —Cys—S—OOC—C$_2$H$_5$ | —H |
| Compound 9  | —Cys—S—OOC—C$_3$H$_7$ | —H |
| Compound 10 | —Cys—S—OOC—C$_4$H$_9$ | —H |
| Compound 11 | —Cys—SH           | —O—C$_2$H$_5$ |
| Compound 12 | —Cys—SH           | —O—C$_3$H$_7$ |
| Compound 13 | —Cys—SH           | —O—C$_4$H$_9$ |
| Compound 14 | —Cys—SH           | —O—C$_5$H$_{11}$ |
| Compound 15 | —Cys—S—O—C$_2$H$_5$ | —H |
| Compound 16 | —Cys—S—O—C$_3$H$_7$ | —H |
| Compound 17 | —Cys—S—O—C$_4$H$_9$ | —H |
| Compound 18 | —Cys—S—O—C$_5$H$_{11}$ | —H. |

3. The salcatonin analogue of claim 1, wherein $R_1$ is -Cys-S—OH or -Cys-S-ester, wherein the ester has from 2 to 5 carbon atoms or pharmaceutically acceptable salts or isomers thereof, and $R_2$ is hydrogen.

4. The salcatonin analogue of claim 1, wherein
$R_1$ is -Cys-S—H, and
$R_2$ is hydroxy or an ester having from 2 to 5 carbons atoms or a pharmaceutically acceptable salt of isomer thereof.

5. A pharmaceutical formula comprising an analogue as claimed in claim 1.

6. A pharmaceutical formula as claimed in claim 5 wherein the analogue is in solution or suspension in a suitable pharmaceutical carrier.

7. A pharmaceutical formula as claimed in claim 6 further comprising sterile water, other sterile liquid, pharmaceutically acceptable excipients or adjuvants or a combination of two or more thereof.

8. A process for the preparation of an analogue as claimed in claim 1 comprising oxidation of salcatonin in the presence of a suitable agent and anhydrous methanol at a temperature in the range of from −10° C. to 20° C. for up to approximately 2½ hours followed by purification.

9. A process as claimed in claim 8 wherein the suitable agent is $H_2O_2$, performic acid, percloric acid, $O_3$, chloranil or a combination of two or more thereof.

10. An analogue as claimed in claim 1 for use in the inhibition of physiological or pathological bone re-absorption.

11. An analogue as claimed in claim 1 for use as a hypocalcemic agent.

12. An analogue as claimed in claim 1 for administration in a daily dose of 10 I.U. to 400 I.U.

13. An analogue as claimed in claim 1 for administration in a daily dose of 100 I.U. to 200 I.U.

14. A process for determining the content of hydroxysalcatonins in a salcatonin preparation comprising comparing the amount of hydroxysalcatonin in the salcatonin preparation to a standard containing a known amount of a hydroxysalcatonin analogue as claimed in claim 1.

15. A process as claimed in claim 14 which is a chromatographic analytical test.

* * * * *

SEQUENCE LISTING

<160> NUMBER OF SEQ ID NOS: 1

<210> SEQ ID NO 1
<211> LENGTH: 32
<212> TYPE: PRT
<213> ORGANISM: salmon
<220> FEATURE:
<221> NAME/KEY: VARIANT
<222> LOCATION: (1)
<223> OTHER INFORMATION: position 1 may encompass a modified Cys residue

<400> SEQUENCE: 1

Xaa Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
            20                  25                  30